United States Patent [19]

Arkles

[11] Patent Number: 4,595,775
[45] Date of Patent: Jun. 17, 1986

[54] N-METHYLHYDRIDOSILAZANES, POLYMERS THEREOF, METHODS OF MAKING SAME AND SILICON NITRIDES PRODUCED THEREFROM

[75] Inventor: Barry C. Arkles, Bristol, Pa.
[73] Assignee: Petrarch Systems, Inc., Bristol, Pa.
[21] Appl. No.: 597,328
[22] Filed: Apr. 6, 1984
[51] Int. Cl.$^4$ .................................................. C07F 7/10
[52] U.S. Cl. ........................................ 556/409; 501/88; 501/97
[58] Field of Search ......................................... 556/409

[56] References Cited

U.S. PATENT DOCUMENTS

| | | | |
|---|---|---|---|
| 2,885,370 | 5/1959 | Groszos et al. | 556/409 X |
| 3,228,895 | 1/1966 | Burks et al. | 556/409 X |
| 3,230,242 | 1/1966 | Fink | 556/409 |
| 3,239,489 | 3/1966 | Fink | 556/409 X |
| 3,393,218 | 7/1968 | Van Wazer et al. | 556/409 X |
| 3,481,964 | 12/1969 | Ismail | 556/409 X |
| 3,655,711 | 4/1972 | Bush et al. | 556/409 |
| 3,892,583 | 7/1975 | Winter et al. | 106/55 |
| 4,200,666 | 4/1980 | Reinberg | 427/39 |

OTHER PUBLICATIONS

Seyferth et al., "A Liquid Silazane Precursor to Silicon Nitride", *Communications of the American Ceramic Society*, p. C-13, (Jan. 1983).

E. G. Rochow, "Polymeric Methylsilazanes", *Organosilicon Chemistry*, pp. 247-262, IUPAC (1965).

*Primary Examiner*—Paul F. Shaver
*Attorney, Agent, or Firm*—Panitch, Schwarze, Jabobs & Nadel

[57] ABSTRACT

Cyclic silazanes which are particularly useful for the formation of silicon nitrides have the general formula:

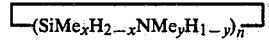

wherein Me represents methyl (CH$_3$), n=3-6, x=0-1 and y=0.25-1. These N-methylhydridosilazanes are a convenient source of silicon nitride by chemical vapor deposition to form films for masking layers and dielectric coatings with reduced levels of silicon carbide contamination in the silicon nitride. Low molecular weight, linear polymers of the N-methylhydridosilazanes are also useful in the preparation of silicon nitrides by evaporation from liquid solutions and subsequent pyrolysis and are particularly useful for infiltration of refractories. Particularly preferred compounds of the invention are 2,6 di-N-methyl-1,3,5,7-tetramethylcyclotetrasilazane; 2,4,6,8-tetra-N-methyl-1,5-dimethylcyclotetrasilazane and their polymeric derivatives.

14 Claims, 3 Drawing Figures

N-METHYLHYDRIDOSILAZANES, POLYMERS THEREOF, METHODS OF MAKING SAME AND SILICON NITRIDES PRODUCED THEREFROM

The present invention relates to novel cyclic silazanes and polymers thereof which may be used to form high quality silicon nitride structures. More particularly the invention relates to N-methylhydridosilazanes and polymer by-products or derivatives thereof.

BACKGROUND OF THE INVENTION

Silicon nitride is an important material for fabrication of masking layers and dielectric coatings for microelectronic devices and the production of high temperature refractories. The fabrication of masking layers and dielectric coatings is commonly accomplished by film deposition, usually from a mixture of silane and ammonia which is decomposed at high temperature. Many operation difficulties are encountered in producing silicon nitride by this method. For example, variables in the rates of reactivity at different temperatures, controlling flow rates of gas mixtures and the pyrophoric nature of silane all contribute to difficulties in preparing silicon nitride films of uniform quality.

One solution proposed to solve these problems was the use of trisilylamine as a source for silicon nitride, as disclosed in U.S. Pat. No. 4,200,666. This volatile precursor for silicon nitride was anticipated to be of utility in preparing films for microelectronics. However, trisilylamine is difficult to prepare and is pyrophoric.

The production of high temperature refractories from silicon nitride suffers from some of the same difficulties. A proposed method which is more appropriate for silicon nitride refractories is disclosed in U.S. Pat. No. 3,892,583, and in a different variation described by Seyferth et al., "A Liquid Silazane Precursor to Silicon Nitride," *Communications of the American Ceramic Society*, page C-13 (January 1983). In these methods a resinous polysilazane of unknown structure is prepared in relatively low yield and then pyrolyzed to form silicon nitride. However, resins of this type, particularly those described by Seyferth et al., suffer from stability problems.

Another potential source for silicon nitride is through the decomposition of cyclic and polymeric diorganosilazanes. These compounds are considered by Zhinkin et al. *Plasticheski Massy* 12:16-17 (1963) and include the class of compounds represented by the following general formula:

wherein R is an organic moiety, particularly alkyl, and n=3-4.

BRIEF SUMMARY OF THE INVENTION

According to the present invention, there has been discovered a new class of cyclic silazanes, namely N-methylhydridosilazanes and polymers thereof, which have been found to be particularly useful in producing high quality silicon nitrides with low silicon carbide contamination and without many of the difficulties encountered in prior art silicon nitride fabrications. The N-methylhydridosilazanes are cyclic compounds having at most only one carbon atom bound to each silicon and a significant proportion of lower bond energy carbon-nitrogen bonds. The cyclic silazanes of the invention are represented by the formula

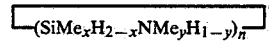

wherein Me represents methyl ($CH_3$), n=3–6, x=0–1 and y=0.25–1. Polymers of the cyclic silazanes are produced as a by-product of the synthesis of the cyclic silazanes or by equilibration of the cyclic silazanes by ammonium salts.

Silicon nitrides may be readily prepared by chemical vapor deposition of the cyclic silazanes or by heating a hydrocarbon solvent solution of a polymeric cyclic silazane to evaporate the solvent and pyrolyze the silazane.

BRIEF DESCRIPTION OF THE DRAWINGS

The foregoing summary, as well as the following detailed description will be better understood when read in conjunction with the appended drawings. For the purpose of illustrating the invention, there is shown in the drawings embodiments which are presently preferred, it being understood, however, that this invention is not limited to the precise arrangements shown. In the drawings.

DETAILED DESCRIPTION OF PREFERRED EMBODIMENT

In contrast to the prior art dialkylsilazanes previously considered as silicon nitride precursors, the N-methylhydridosilazanes of the present invention contain at most only one carbon bound to each silicon. These cyclic silazanes have alternating silicon and nitrogen atoms forming the ring structure with one methyl group and one hydrogen atom or two hydrogen atoms on the silicons and a methyl group or hydrogen atom on the nitrogens. The rings may contain from three to six silicon atoms and from three to six nitrogen atoms in alternating sequence around the ring and preferably three or four silicon and three or four nitrogen atoms per ring.

Figure 1:
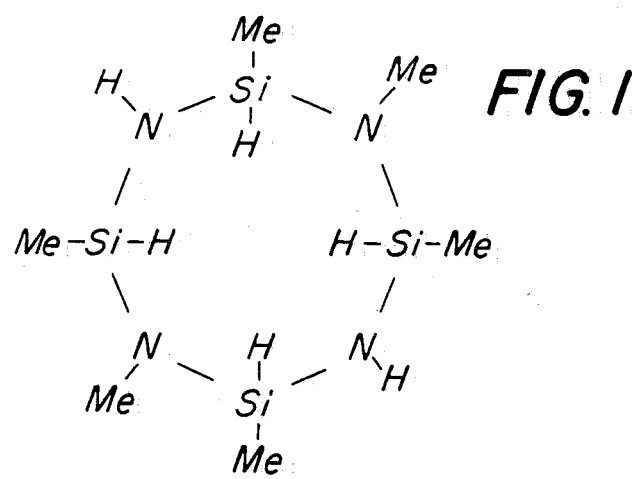
FIG. 1 is a structural formula of 2,6 di-N-methyl-1,3,5,7-tetramethylcyclotetrasilazane.
Figure 2:
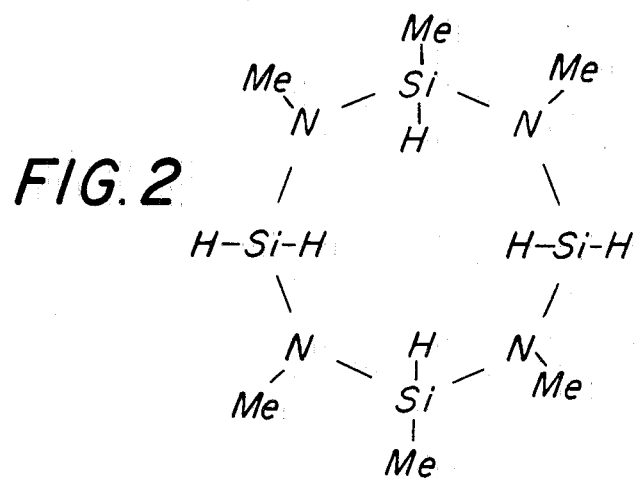
FIG. 2 is the structural formula for 2,4,6,8 tetra-N-methyl-1,5-dimethylcyclotetrasilazane.

The N-methylhydridosilazanes of the present invention which are particularly preferred as precursors of silicon nitride are the hexamethylcyclotetrasilazanes, namely 1,2,3,5,6,7-hexamethylcyclotetrasilazane (2,6 di-N-methyl-1,3,5,7 tetramethylcyclotetrasilazane) and 1,2,4,5,6,8-hexamethylcyclotetrasilazane (2,4,6,8 tetra-N-methyl-1,5 dimethylcyclotetrasilazane). The structures of these two compounds are shown in FIGS. 1 and 2, respectively.

For the preferred hexamethylcyclotetrasilazanes, a stoichiometric balance exists which may be expressed by the following equation:

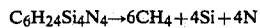

This equation is not meant to indicate any reactive paths or products, and methane is not cleanly produced. However, as seen from the above formula, there is a 4:1 ratio of hydrogen to carbon in the molecules, which appears to favor the driving off of carbons or organic moieties as methane. These compounds also have a lower ratio of carbon to silicon than exists in the diorganosilazanes.

Silicon nitride is generally taken to be $Si_3N_4$ on the average, although chemical analysis varies and the exact makeup of silicon nitride films is largely process dependent. While not wishing to be bound by any particular theory, it is believed that the efficacy of the N-methyl-hydridosilazanes of the present invention in decomposing to silicon nitride when compared to the diorganosilazanes is probably related to the lower bond energy of carbon-nitrogen bonds as compared to the bond energy of carbon-silicon bonds. Moreover, the enhanced stability of the N-methylhydridosilazanes when compared to the compounds reported by Seyferth, et al., supra, is probably due to the reduced ability of the N-methylhydridosilazanes to crosslink by loss of hydrogen molecules.

It is evident from the above equation that if silicon nitride is $Si_3N_4$, there will be silicon atoms not bound to nitrogen, and therefore likely to be present in the form of silicon carbides. This stoichiometric balance does not work out nearly as well for the prior art diorganohexamethyltrisilazanes in which there are two methyl groups bound to each silicon atom in the ring. However, as will be shown in the examples below, the hexamethyltrisilazane which falls within the present invention, namely 2,4,6 tri-N-methyl-1,3,5 trimethylcyclotrisilazane, in which there is one methyl group on each silicon atom and one methyl group on each nitrogen atom in the ring, produces silicon nitride having a much lower silicon carbide contamination than the corresponding diorganohexamethyltrisilazane.

The N-methylhydridosilazanes of the present invention are formed by reacting methyldichlorosilane with methylamine in the presence of a basic receptor such as a tertiary amine, e.g., triethylamine, and a hydrocarbon solvent such as pentane, to form trimethyl intermediates which are then reacted with ammonia or dichlorosilane to yield the cyclic silazanes. The chemistry of the reaction and the stoichiometry of the reactants controls the ring size. Generally, if a single amine is reacted with a single dichlorosilane, a mixture is obtained in which n=3 and 4, and a residue of low molecular weight, generally linear polymers is obtained in which n is greater than 6. Such polymers have not been completely characterized, but they are not highly crosslinked and the chemical groups (which are the same as those of the cyclic N-methylhydridosilazanes) have been identified by infrared spectroscopy. These polymers are probably analogous to the polymeric methylsilazanes described by E. C. Rochow in the chapter "Polymeric Methylsilazanes" in *Organosilicon Chemistry*, pages 247-262, IUPAC (1965).

The preparation of the cyclic N-methylhydridosilazanes of the present invention may be illustrated by the following three reaction equations. 2,4,6 tri-N-methyl-1,3,5 trimethylcyclotrisilazane is prepared by the reaction:

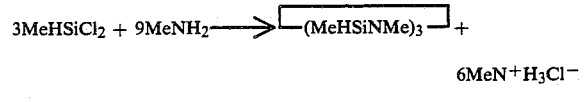

2,6 di-N-methyl-1,3,5,7 tetramethylcyclotetrasilazane may be prepared according to the following two-step reaction:

Step 1:

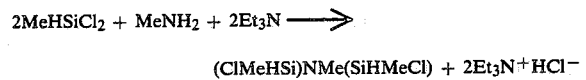

Step 2:

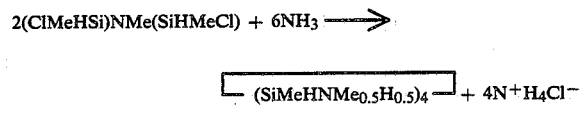

(See FIG. 1)

2,4,6,8 tetra-N-methyl-1,5-dimethylcyclotetrasilazane may be prepared by the following two-step reaction equation:

Step 1:

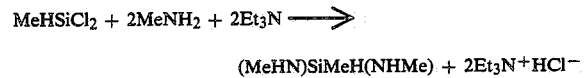

Step 2:

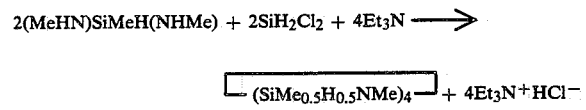

(See FIG. 2)

It will be understood that the above reaction equations are greatly simplified stoichiometric relationships which represent the primary reactions taking place, but do not take into account the formation of minor fractions due to side reactions, etc. Moreover, the above equations do not identify all of the reaction conditions, nor the need in some cases to use excess amounts of some reactants to insure complete reaction. However, those of ordinary skill in the art will readily understand the practice of the invention from the above equations and the more specific examples set forth below.

The reactions are carried out under chilled conditions, preferably $-30$ to $-50$ degrees Centigrade, which may be achieved with a dry ice/acetone bath. Afer reaction of all of the chlorosilanes and removal of amine hydrochloride salts from the reaction mixture by filtration, the hydrocarbon solvent is stripped from the mixture, and the remainder of the mixture is distilled to yield the N-methylhydridosilazanes.

The preferred hexamethylcyclotetrasilazanes of the present invention are volatile liquids with boiling points in the range 200-210 degrees C. at atmospheric pressure. They are stable when stored at room temperature under a dry nitrogen atmosphere. Most importantly, they are a convenient source for producing uniform quality silicon nitride by chemical vapor deposition, which may be carried out in conventional manners known in the art, such as heating to temperatures on the order 350 degrees C. under an inert atmosphere, such as dry nitrogen, which may also include ammonia.

As noted above, by-products of the synthesis of the cyclic silazanes of the present invention are the polymeric derivatives of these silanes. These polymeric derivatives are believed to be essentially linear in nature, and can also be produced by equilibration of the cyclic silazanes with ammonium salts such as ammonium chloride. For example 5% by weight NH₄Cl added to a cyclic silazane and agitated for about 4-24 hours above about 150 degrees C. will yield the polymeric derivatives.

These higher boiling polymeric silazanes are particularly useful for infiltration of refractories which may be subsequently "fired" at high temperatures to yield silicon nitride impregnated refractories. Deposition of silicon nitride from such polymeric silazanes may be accomplished from a solution of the polymeric silazanes in a hydrocarbon solvent such as xylene by evaporating the solvent and then heating to temperatures on the order of 450 degrees C. under an inert atmosphere, such as dry nitrogen to decompose the silazane by pyrolysis.

Polymeric silazanes of the present invention include, but are not limited to, low molecular weight polymers obtained as by-products of the synthesis of 2,6 di-N-methyl-1,3,5,7 tetramethylcyclotetrasilazane; 2,4,6,8 tetra-N-methyl-1,5 dimethylcyclotetrasilazane; and 2,4,6 tri-N-methyl-1,3,5 trimethylcyclotrisilazane.

The invention will now be described in more detail with reference to the following specific, non-limiting examples:

EXAMPLE I

Preparation of 2,6 di-N-methyl-1,3,5,7 tetramethylcyclotetrasilazane

A two-liter, four-neck flask was equipped with a mechanical stirrer, addition funnel, dry-ice/acetone dewar condensor and a low temperature thermometer. The flask was charged with 1,000 ml of pentane and 2 moles (230 g) of methyldichlorosilane. The mixture was chilled in a dry-ice/acetone bath until the temperature reached −50 degrees C. Addition of 2 moles of triethylamine was made rapidly and the temperature was allowed to return to −50 degrees C. White salts associated with triethylamine-methyldichlorosilane complex were observed.

At this point, the addition funnel was removed and replaced by a gas inlet tube through which 1 mole (30 g) of methylamine was added. The temperature was allowed to rise to −30 degrees C. during the addition. The mixture was then stirred for 20 to 30 minutes at −30 degrees C. then allowed to rise to about 0 degrees C. and stirred for one more hour.

The temperature was again reduced to −50 degrees C., and an excess of ammonia was added until it refluxed indicating complete reaction. The mixture was allowed to return to room temperature and stirred for four hours. The amine hydrochloride salts were removed from the reaction mixture by filtration through a fiberglass filter tube. The clear mixture was purged briefly with ammonia to confirm that all chlorosilanes had reacted. (Unreacted silanes are indicated by cloudiness or precipitation.)

The mixture was stripped free of pentane and distilled under ammonia at atmospheric pressure. A main fraction with a 185-220 degrees C. boiling range was recovered. The flask retained 60 g of low molecular weight polymer. Redistillation of the main cut gave 40 g of a fraction with a boiling range of 202-206 degrees C. which was shown by gas chromotography to contain 87% of a single component. IR spectra showed very characteristic silicon-hydrogen absorptions at 2100 and a broad amine absorption. The ratio of proton NMR strength associated with methyl bound to silicon and methyl bound to nitrogen was 2.1:1. This evidence for the 87% peak is consistent with the proposed structure of the title compound, namely 2,6 di-N-methyl-1,3,5,7 tetramethylcyclotetrasilazane.

The pot fraction was refiltered to remove small amounts of unidentified solids. In the material the relative absorption in the IR due to silicon hydrogen was slightly reduced.

EXAMPLE II 2,4,6,8 tetra-N-methyl-1,5-dimethylcyclotetrasilazane

Under conditions similar to those described in Example I, 1 liter of pentane and 4 moles (405 g) of triethylamine were charged to a four-neck, two-liter flask and chilled to −50 degrees C. Two moles (30 g) of methylamine was inletted, followed by the slow addition of 1 mole (115 g) of methyldichlorosilane. The mixture was stirred while the temperature was allowed to rise to −10 degrees C. over four hours. The mixture was chilled to −50 degrees C. again and 1 mole (101 g) of dichlorosilane was added. The mixture was stirred for four hours, during which time the temperature rose to 0 degrees C.

The mixture was filtered immediately, the pentane was stripped off and 35 g of a main fraction was recovered under vacuum distillation (bp 72-78 degrees C./8-9 mm Hg). The mixture was 81% of a single component which was identified by IR as the title compound, namely 2,4,6,8 tetra-N-methyl-1,5-dimethylcyclotetrasilazane. The pot contained a 40 g residue.

EXAMPLE III

Silicon nitride deposition from N-methylhydridosilazanes

Figure 3:
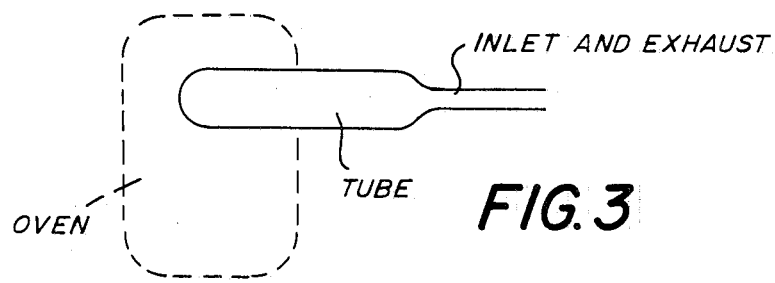
FIG. 3 is a schematic illustration of a simple apparatus used for performing chemical vapor deposition of silicon nitride from cyclic silazanes (see Example III below).

For these experiments an apparatus schematically depicted in FIG. 3 was used to form silicon nitride by chemical vapor deposition. The apparatus comprises a 150 mm borosilicate test tube, one end of which was drawn down to a tube with an ID of 4-6 mm. The large end of the tube was placed in a "muffle" oven and heated to 350 degrees C. The narrow open end extended outside the oven. The tube was purged briefly with ammonia by means of a micropipette.

For each of the four experiments about 5 ml of the indicated cyclosilazane was slowly injected into the tube through a long stainless steel needle and heated for approximately one hour. The entire experiment was conducted in a hood. After completion of the deposition, the end of each tube was cooled, broken and the brown residues were scraped and subjected to elemental analysis. The results are report in Table 1 below and are based on a conversion analysis of carbon and nitrogen content.

TABLE 1

| Chemical Compound | % Silicon Nitride | % Silicon Carbide |
|---|---|---|
| 1,1,3,3,5,5 hexamethyl-cyclotrisilazane (control) | 30-40% | 60-70% |
| 2,4,6 tri-N—methyl-1,3,5 trimethylcyclotrisilazane | 50-60% | 40-50% |
| 2,6 di-N—methyl-1,3,5,7 tetramethylcyclotetrasilazane | 80-85% | 15-20% |
| 2,4,6,8 tetra-N—methyl-1,5 | 85-90% | 10-15% |

TABLE 1-continued

| Chemical Compound | % Silicon Nitride | % Silicon Carbide |
|---|---|---|
| dimethylcyclotetrasilazane | | |

EXAMPLE IV

Silicon nitride from N-methylhydridosilazane polymers

In these experiments, the polymeric residues from the preparation of Example I and a polymer prepared by equilibrating the compound of Example I with ammonium chloride were used. In each case, the polymer ws diluted 5:1 in xylene. The resulting solutions were applied to separate 4 inch silicon wafers by a spin-on technique. Under a dry nitrogen atmosphere, the wafers were heated to 175 degrees C. for one hour to remove the xylene and then heated to 450 degrees C. for four hours. The residues were identified by Auger Spectroscopy as predominantly silicon nitride.

It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

I claim:

1. A cyclic silazane of the formula:

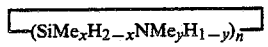

wherein Me represents methyl ($CH_3$), $n=3-6$, $x=0-1$ and $y=0.25-1$.

2. A cyclic silazane according to claim 1 wherein $n=3$.

3. A cyclic silazane according to claim 1 wherein $n=4$.

4. 2,6 di-N-methyl-1,3,5,7 tetramethylcyclotetrasilazane.

5. 2,4,6,8 tetra-N-methyl-1,5 dimethylcyclotetrasilazane.

6. 2,4,6 tri-N-methyl-1,3,5 trimethylcyclotrisilazane.

7. Polymeric derivatives of the cyclic silazanes of claim 1 produced by equilibration of said cyclic silazanes with an ammonium salt.

8. A method of producing the cyclic silazane of claim 4 and polymeric derivatives thereof comprising reacting methyldichlorosilane with methylamine in the presence of a basic receptor and a hydrocarbon solvent under chilled conditions, adding ammonia to the reaction mixture, filtering out amine hydrochlorides, stripping the solvent from the mixture and distilling the remainder to yield said cyclic silazane and polymeric derivatives thereof.

9. A method of producing the cyclic silazane of claim 5 and polymeric derivatives thereof comprising reacting methyldichlorosilane with methylamine in the presence of a basic receptor and a hydrocarbon solvent under chilled conditions, adding dichlorosilane to the reaction mixture, filtering out amine hydrochlorides, stripping the solvent from the mixture and distilling the remainder to yield said cyclic silazane and polymeric derivatives thereof.

10. A method according to claims 8 or 9 wherein said basic receptor is triethylamine and said solvent is pentane.

11. Polymeric derivatives produced as a byproduct of the methods of claims 8 or 9.

12. Poly 2,6 di-N-methyl- 1,3,5,7 tetramethylcyclotetrasilazane.

13. Poly 2,4,6,8 tetra-N-methyl-1,5 dimethylcyclotetrasilazane.

14. Poly 2,4,6 tri-N-methyl-1,3,5 trimethylcyclotrisilazane.

* * * * *